(12) United States Patent
Kautzky

(10) Patent No.: US 7,879,615 B2
(45) Date of Patent: *Feb. 1, 2011

(54) HEMOSTASIS ANALYZER AND METHOD

(75) Inventor: Hans Kautzky, West Chicago, IL (US)

(73) Assignee: Coramed Technologies, LLC, Niles, IL (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/425,818

(22) Filed: Jun. 22, 2006

(65) Prior Publication Data

US 2007/0092405 A1 Apr. 26, 2007

Related U.S. Application Data

(60) Provisional application No. 60/728,505, filed on Oct. 20, 2005.

(51) Int. Cl.
*G01N 33/86* (2006.01)

(52) U.S. Cl. .................. 436/69; 436/63; 422/73; 600/369; 73/64.41; 73/64.42

(58) Field of Classification Search ............ 436/63, 436/69, 150, 164, 165; 422/73, 82.01, 82.05; 600/369; 73/64.41, 64.42, 64.43
See application file for complete search history.

(56) References Cited

U.S. PATENT DOCUMENTS

| 3,741,002 | A | * | 6/1973 | Simons ............... 73/64.53 |
|---|---|---|---|---|
| 3,854,324 | A | | 12/1974 | Altshuler et al. |
| 4,149,405 | A | | 4/1979 | Ringrose |
| 4,202,204 | A | | 5/1980 | Hartert |
| 4,341,111 | A | | 7/1982 | Husar |
| 4,695,956 | A | | 9/1987 | LeVeen et al. |
| 5,075,077 | A | | 12/1991 | Durley, III et al. |
| 5,096,669 | A | | 3/1992 | Lauks et al. |
| 5,100,805 | A | | 3/1992 | Ziege et al. |
| 5,114,860 | A | | 5/1992 | Hayashi |
| 5,167,145 | A | | 12/1992 | Butler et al. |
| 5,223,227 | A | * | 6/1993 | Zuckerman ............ 422/102 |
| D337,164 | S | | 7/1993 | Lauks et al. |
| 5,416,026 | A | | 5/1995 | Davis |
| 5,447,440 | A | | 9/1995 | Davis et al. |
| 5,494,639 | A | * | 2/1996 | Grzegorzewski ........ 422/82.01 |
| 5,534,226 | A | | 7/1996 | Gavin et al. |
| 5,580,744 | A | | 12/1996 | Zweig |

(Continued)

FOREIGN PATENT DOCUMENTS

JP 58-39926 * 3/1983

(Continued)

OTHER PUBLICATIONS

Voleisis et al., "Ultrasonic method for the whole blood coagulation analysis," Ultrasonics, vol. 40, May 2002, pp. 101-107.

*Primary Examiner*—Maureen M Wallenhorst
(74) *Attorney, Agent, or Firm*—Anthony G. Sitko PLC

(57) ABSTRACT

A method and device for blood hemostasis analysis is disclosed. A blood sample is displaced to reach a resonant state. The resonant frequency of the blood sample is determined before, during and after a hemostasis process. The changes in the resonant frequency of the blood sample are indicative of the hemostasis characteristics of the blood sample.

8 Claims, 9 Drawing Sheets

U.S. PATENT DOCUMENTS

| | | |
|---|---|---|
| 5,628,961 A | 5/1997 | Davis et al. |
| 6,060,323 A | 5/2000 | Jina |
| 6,066,504 A | 5/2000 | Jina |
| 6,136,271 A | 10/2000 | Lorincz et al. |
| 6,196,979 B1 | 3/2001 | Virtanen |
| 6,200,532 B1 | 3/2001 | Wu et al. |
| 6,327,031 B1 | 12/2001 | Gordon |
| 6,338,821 B1 | 1/2002 | Jina |
| 6,438,498 B1 | 8/2002 | Opalsky et al. |
| 6,524,861 B1 | 2/2003 | Anderson |
| 6,706,536 B1 * | 3/2004 | Carroll et al. ............... 436/164 |
| 7,261,861 B2 * | 8/2007 | Kautzky ...................... 422/73 |

FOREIGN PATENT DOCUMENTS

| | | |
|---|---|---|
| WO | WO-01/96879 A2 | 12/2001 |

* cited by examiner

US 7,879,615 B2

HEMOSTASIS ANALYZER AND METHOD

FIELD OF THE DISCLOSURE

This disclosure relates generally to blood analysis, and more particularly, to a blood hemostasis analyzer and method.

BACKGROUND

Blood is in liquid form when traveling undisturbed in bodily passageways. However, an injury may cause rapid clotting of the blood at the site of the injury to initially stop the bleeding, and thereafter, to help in the healing process. An accurate measurement of the ability of a patient's blood to coagulate in a timely and effective fashion and subsequently to lyse is crucial to certain surgical and medical procedures. Also, accurate detection of abnormal hemostasis is of particular importance with respect to appropriate treatment to be given to patients suffering from clotting disorders.

Blood hemostasis is a result of highly complex biochemical processes that transform the blood from a liquid state to a solid state. Characteristics of blood, such as strength of the clot, infer that the mechanical properties of the blood are important in determining characteristics rather than the viscosity of the blood when in a liquid state.

DETAILED DESCRIPTION

Figure 1:
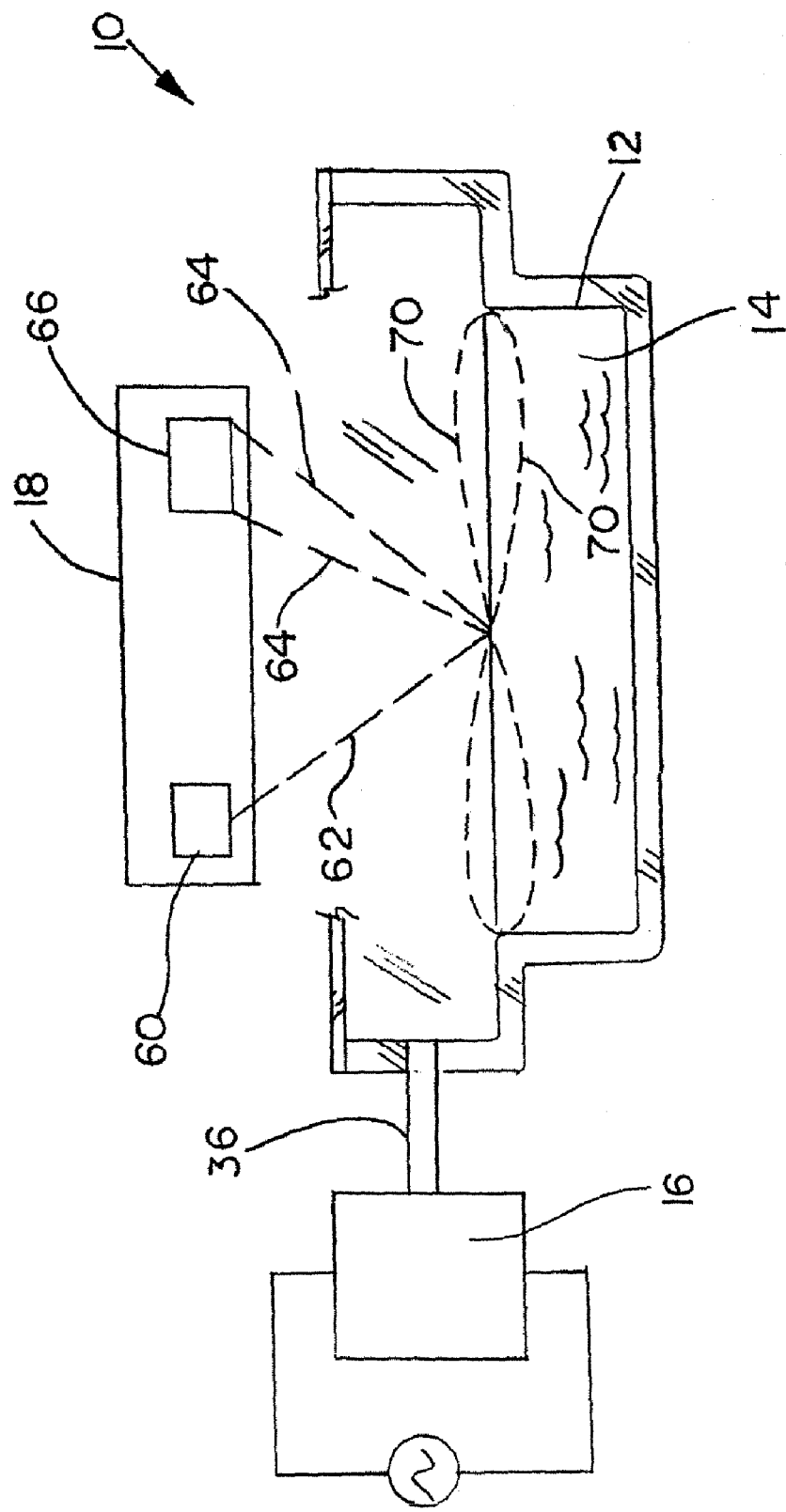
FIG. 1 is a schematic diagram of a blood hemostasis analyzer constructed in accordance with the teachings of the instant disclosure.

Referring to FIG. 1, a blood hemostasis analyzer 10 in accordance with the teachings of the instant disclosure is generally shown. The analyzer 10 operates under the principle that because hemostasis of a blood sample changes the blood sample from a liquid state to a gel-like state, and the modulus of elasticity of the blood sample controls the natural frequency of the blood sample, measuring the changes in the natural frequency of the blood sample during hemostasis provides the hemostasis characteristics of the blood sample. In keeping with this principle, the disclosed blood hemostasis analyzer 10 measures the changes in the fundamental natural frequency of a blood sample during hemostasis and lysis processes to provide hemostasis characteristics of the blood sample. To measure hemostasis in this manner, the analyzer 10 generally includes a container 12 for holding a blood sample 14, a shaker 16 for displacing the container 12 to thereby excite the blood sample 14 to a resonant vibration, and a sensor 18 for measuring the resulting amplitude of the blood sample 14.

An exemplary method by which the disclosed blood hemostasis analysis is also described. Vibration of a liquid at resonance closely resembles sloshing, which is analogous to the motion of a pendulum. Accordingly, as blood transitions from a liquid state to a gel-like state and possibly to a solid state during clotting, the fundamental natural frequency of the blood increases. The disclosed exemplary method measures the changes in the fundamental natural frequency of the blood sample 14 during hemostasis/clotting and lysis processes.

Initially, a blood sample 14 is placed in the container 12. The container 12 is then vibrated by the shaker 16 so that the blood sample 14, which is initially in a liquid state, is vibrating in a sloshing mode. A liquid typically vibrates near its first fundamental natural frequency in a sloshing mode, which can be defined as the swinging of the entire mass of the liquid in a container, hence the analogy to a pendulum. The amplitude of the sloshing reaches maximum when the blood sample 14 is vibrated at its fundamental natural frequency. Thus, to initially excite the blood sample 14 to resonance, the shaker 16 vibrates the container 12 at or very near the fundamental natural frequency of the blood sample 14. Furthermore, the shaker 16 vibrates the container 12 at or very near the fundamental natural frequency of the blood sample 14 as this frequency changes throughout the hemostasis and possibly lysis processes.

One of ordinary skill in the art will readily appreciate the numerous methods by which the shaker 16 can be made to vibrate the container 12 at or near the fundamental natural frequency of the blood sample 14 throughout the hemostasis and lysis processes. However, in the disclosed example, the container 12 is initially vibrated at a frequency below the fundamental natural frequency of the blood sample 14. The frequency is then increased in small steps, and concurrently, the resulting displacement amplitudes of the blood sample 14 are measured. As the frequency of vibration of the container 12 increases to near the blood sample's fundamental natural frequency, the displacement amplitude of the blood sample 14 will dramatically increase. The displacement amplitude of the blood sample 14 will reach maximum at its fundamental natural frequency. Thus, monitoring the displacement amplitude of the blood sample 14 for a maximum provides a value for the fundamental natural frequency of the blood sample 14 when that maximum is reached.

Figure 2:
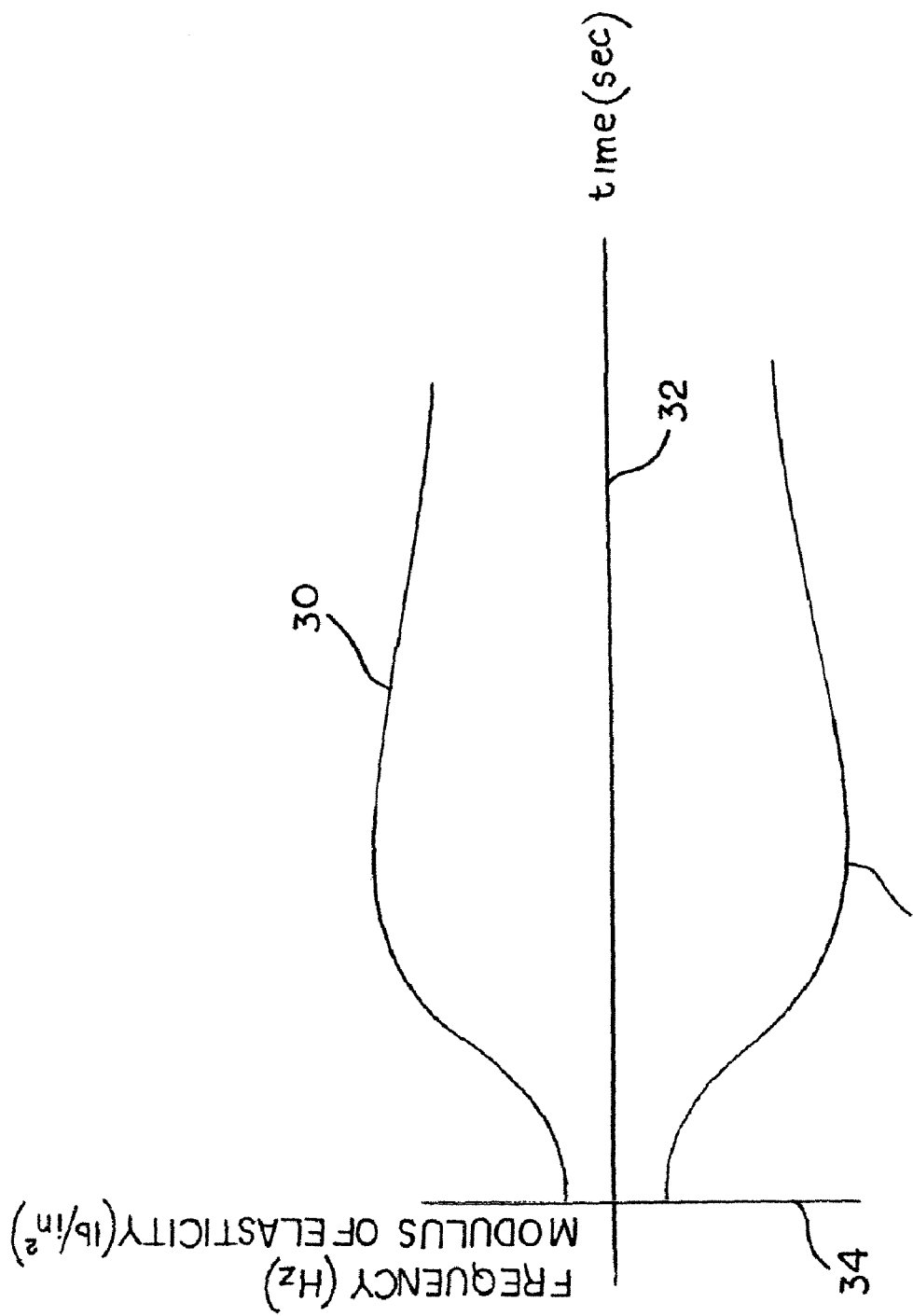
FIG. 2 is a graph representing hemostasis characteristics of a blood sample in accordance with the teachings of the instant disclosure.

As the hemostasis process continues, the foregoing method of finding the fundamental natural frequency of the blood sample 14 is repeated. The measured fundamental natural frequencies of the blood sample 14 when plotted vs. time result in a curve 30 similar to that shown in FIG. 2. Curve 30 is typically represented with its mirror image relative to the x-axis, which is shown as curve 31. The shape of the curve 30 is indicative of blood hemostasis characteristics. The x-axis 32 represents time, while the y-axis 34 represents the fundamental natural frequency of the blood sample 14 during the hemostasis and lysis processes. One of ordinary skill in the art will appreciate that since frequency of the blood sample 14 is proportional to the modulus of elasticity of the blood sample 14, the y-axis also represents the changes in the modulus of elasticity of the clotted blood sample 14 during hemostasis and lysis processes.

One of ordinary skill in the art will readily appreciate that the size of the frequency step by which the vibration frequency of the container 12 is increased or decreased during testing will affect how quickly and efficiently the fundamental natural frequency of the blood sample 14 is pinpointed. For instance, a very large frequency step may not provide a detailed frequency resolution to locate a near accurate measure of the fundamental natural frequency of the blood sample 14. On the other hand, a very small frequency step may not provide a rapid approach to pinpointing the fundamental natural frequency of the blood sample 14. Accordingly, in order to find the fundamental natural frequency of the blood sample within the frequency range by which the container 12 is vibrated, it may be necessary to search for the fundamental natural frequency of the blood sample 14 by changing the frequency step and/or adding or subtracting the frequency step from the vibration frequency of the container 12 in a methodical manner. Numerous mathematical algorithms and methods are well known to those of ordinary skill in the art, by which the frequency step can be methodically varied to provide a rapid pinpointing of a peak in amplitude of oscillation of the blood sample 14.

One of ordinary skill in the art can use other well known methods for finding the fundamental natural frequency of the blood sample throughout the hemostasis and lysis processes. For example, displacing the container 12 with a frequency function that emulates white noise having frequency components near or equal to the fundamental natural frequencies of the blood sample 14 throughout the hemostasis and lysis processes can excite the blood sample 14 to a resonant state. White noise is a frequency function that includes frequency components selected within a range of frequencies. Because the blood sample will respond with resonant excitation to a frequency that is equal or near its fundamental natural frequency, a white noise having such a frequency component will excite the blood sample 14 to a resonant state. One of ordinary skill in the art will readily appreciate that well known methods such as Fourier Frequency Analysis can be utilized to find the fundamental frequency of the blood sample 14 after being excited by white noise.

An exemplary device employing the foregoing method of determining hemostasis characteristics of a blood sample 14 will now be described. Referring to FIG. 1, the shaker 16 displaces the container 12 to excite the blood sample 14 to resonant vibration. Generally, the shaker 16 is a device capable of oscillating the container 12 with a desired frequency and amplitude. One of ordinary skill in the art will appreciate the numerous devices by which an object can be oscillated. In the disclosed example, the shaker 16 is a dipcoil, which is similar to a voice coil of a speaker. In other words, the shaker 16 includes an electromagnetic coil that oscillates relative to a stationary permanent magnet by having the coil current driven by an electrical signal. The shaker 16 may be connected either directly or with a connecting link 36 to the container 12. The connecting link 36 transfers the motion created by the shaker 16 to the container 12. As is well known to those of ordinary skill in the art, characteristics of the electrical signal, i.e., voltage, current, direction of current, etc., determine the characteristics of the oscillatory motion of the shaker 16. Accordingly, the shaker 16 can displace the container 12 with any desired amplitude and frequency within the operational limits of the shaker 16.

The container 12 holds the blood sample 14 during the excitation of the blood sample 14. The container 12 may be any shape or size. However, the shape and size of the container may affect the operation of the analyzer 10, because the container 12 acts as a resonator. The larger the container 12, the lower the natural frequency of the blood sample 14 will be. Furthermore, the container 12 cannot be too small so that an excessive meniscus effect is produced due to the surface tension in the blood sample 14 that may interfere with measuring the oscillating/sloshing motion of the sample within the container 12. Conversely, if the container 12 is too large, a large blood sample 14 will be needed for the analysis in the analyzer 10, which may not be medically acceptable.

Figure 3:
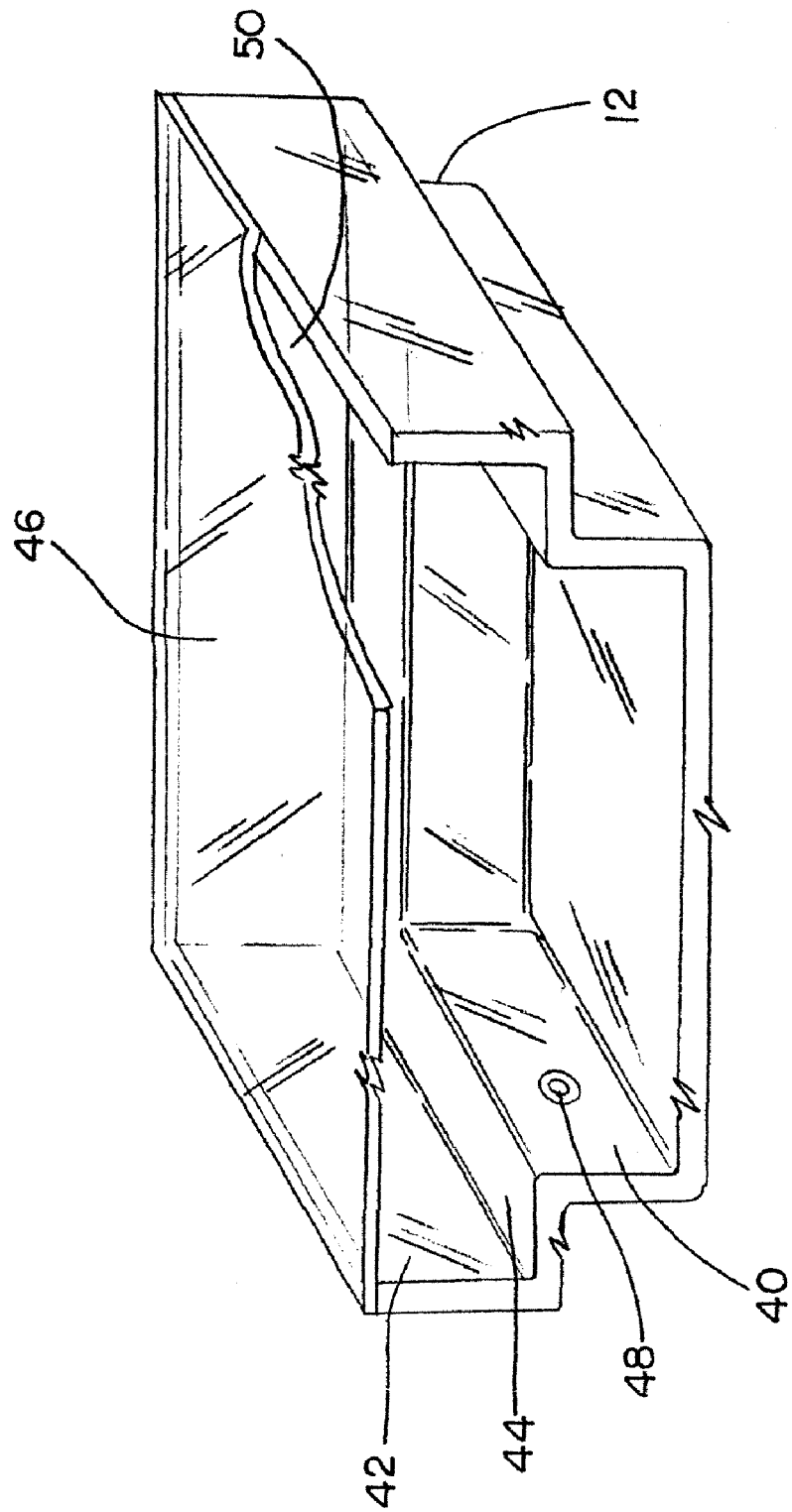
FIG. 3 is a perspective and exploded sectional view of a container for holding a blood sample in accordance with the teachings of the instant disclosure.

An exemplary container 12 is shown in FIG. 3. The container 12 has a lower portion 40 and an upper portion 42. The lower portion 40 and the upper portion 42 are generally rectangular. The upper portion 42 has a larger width, a larger length, and a smaller depth than the lower portion 40, so as to provide an internal step 44. The container 12 also includes a lid 46 that is sealably attached to the top of the upper section 40. The container 12 includes a port 48 for receiving a blood sample 14. To provide a relatively flat, mirror-like upper surface of the blood sample 14 when placed in the container 12, the lower portion 40 is filled with the blood sample up to where the upper portion 42 begins. Accordingly, the volume of the blood sample 14 is substantially equal to the volume of the lower portion 40.

To prevent the blood sample 14 from evaporating during testing and to prevent contamination thereof, the port 48 may be self sealing. For example, the port 48 may be constructed from rubber or silicon so that when a syringe needle is inserted therein, the rubber or silicon resiliently surrounds the syringe needle to substantially seal the port during the injection of the blood sample 14 into the container 12. When the needle is withdrawn from the port 48, resilience of the rubber or the silicon substantially re-seals the hole created by the needle. To prevent evaporation of the blood sample 14 by being exposed to dry air, the container 12 can be pre-filled with an amount of liquid water or water vapor to create a higher level of humidity with the container. In the example disclosed herein, the container 12 is safely disposable and can be safely discarded after each use. The disposability of the container 12 ensures that the blood sample 14 is safely handled during testing and safely discarded after testing. In addition, the disposable container 12 can be manufactured to be completely sealed and only provide access thereto by the port 48. Thus, the disposability of the container 12, combined with the container 12 being completely sealed, ensure that the blood sample 14 is not exposed to dry air (i.e., to prevent the drying of the surface of the blood sample 14) or any other contaminants, and furthermore, ensure safety in handling and disposing of the blood sample 14 before, during, and after testing.

The analyzer 10 includes a slot (not shown) to receive the container 12. One of ordinary skill in the art will readily appreciate that the container 12 may be inserted in and removed from the slot in any manner desirable. However, to provide easy insertion and removal of the container 12 from the analyzer 10, the container 12 may include a handle (not shown) that can be held by a user for insertion and removal of the container 12 to and from the analyzer 10, respectively.

To measure oscillations of the blood sample 14 as a result of the displacement of the container 12, a fixed electromagnetic source 60 emits a beam 62 toward the blood sample 14. As shown in FIG. 1, the source 60 may be part of the sensor 18

(i.e., an active sensor). Alternatively, the source 60 and a sensor 66 (i.e., a passive sensor) can be independent devices. The beam 62 is detected by the sensor 18 after being reflected from the surface of the blood sample 14. The characteristics of the beam after being reflected from the surface of the blood sample 14 are indicative of the movement of the blood sample 14 in response to displacements of the container 12.

One of ordinary skill in the art will appreciate that the electromagnetic beam of the source 60 may be produced by any emission within the electromagnetic spectrum so long as the beam 62 can reflect from the surface of the blood sample 14, and the beam's characteristics after reflecting from the surface of the blood sample 14 indicate the movement of the blood sample 14.

In the disclosed example, the source 60 is a fixed LED (Light Emitting Diode) source that directs a beam 62 towards the blood sample 14. The beam 62 is then reflected from the surface of the blood sample 14. Accordingly, the container 12 has portion transparent to the beam 62 and its reflection 64 so that they can enter and exit the container 12, respectively. In the disclosed example, the enclosure 46 is transparent to light. One of ordinary skill in the art will recognize that the enclosure 46, although transparent, will itself reflect some of the light in the beam 62. To reduce the reflection of light from the lid 46, an anti-reflective coating may be applied to the lid 46. Such anti-reflective coatings are well known to those of ordinary skill in the art as they are applied to a variety of optical devices, such as eyeglasses, telescopes, cameras, etc. Although most liquids are highly transparent to light, the surface of blood forms a highly reflective surface so that most of the beam 62 is reflected from the surface of the blood sample 14.

Figure 4:
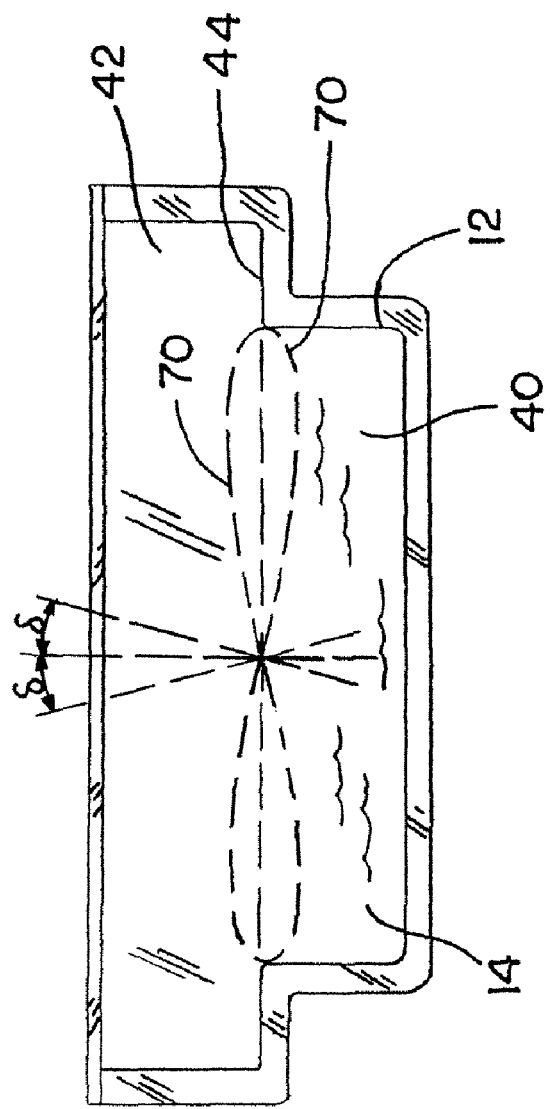
FIG. 4 is a schematic view of the container of FIG. 3 having therein a blood sample and vibrating the blood sample in accordance with the teachings of the instant disclosure.

Referring to FIG. 4, the displacements of the blood sample 14 relative to a rest position are shown with dashed lines 70 having an angle $\theta$. Accordingly, the displacement of the blood sample 14 changes the angle of the reflection 64 of the beam 62 by the same angle $\theta$. The sensor 18 intercepts the reflection 64 of the beam 62 from the surface of the blood sample 14 and produces an electric signal indicative of the displacement of the blood sample 14. In the disclosed example, the sensor 18 includes a plurality of photo diodes that collectively detect the displacement of the reflection of the beam 64. The outputs of the diodes may be measured differentially so that peaks in the displacement of the blood sample 14, which are indicative of resonance, can be identified.

Figure 5:
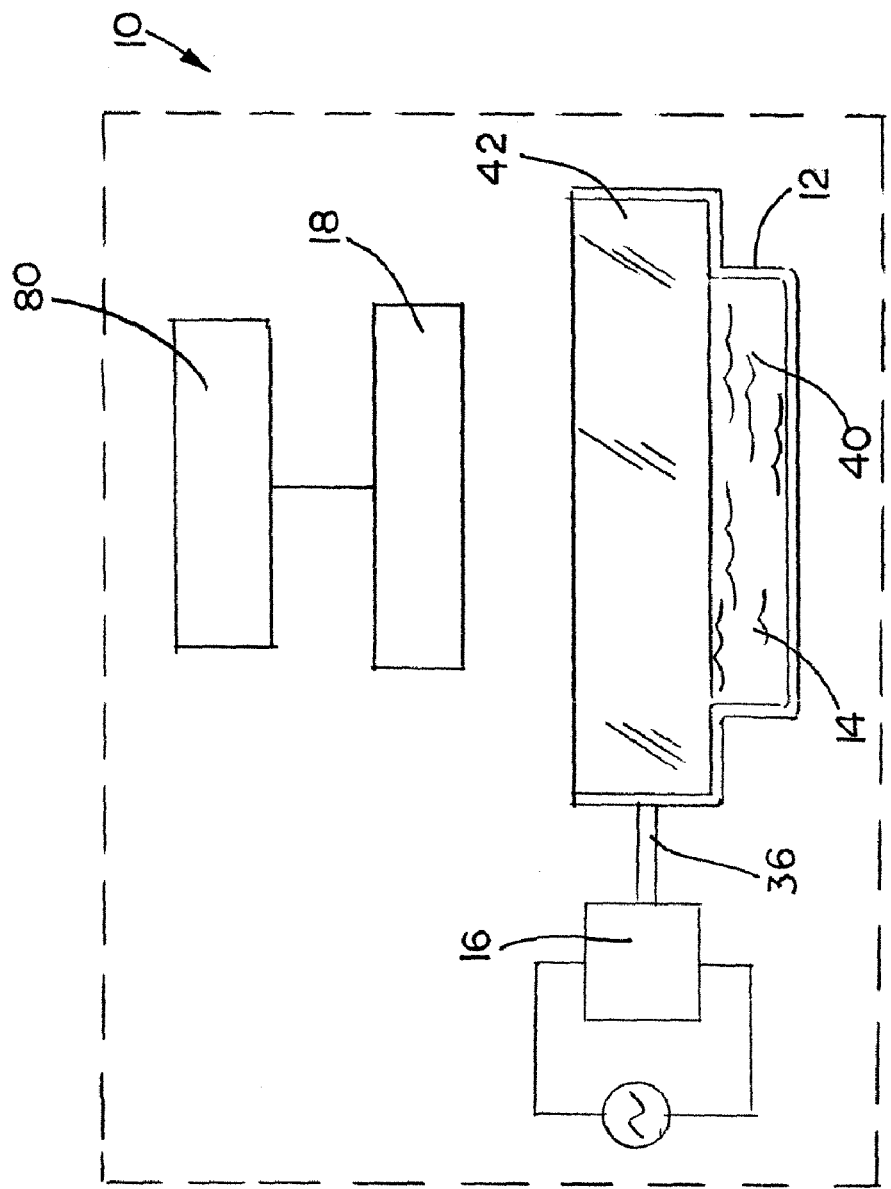
FIG. 5 is a schematic view of an analyzer in accordance with the teachings of the instant disclosure.
Figure 6:
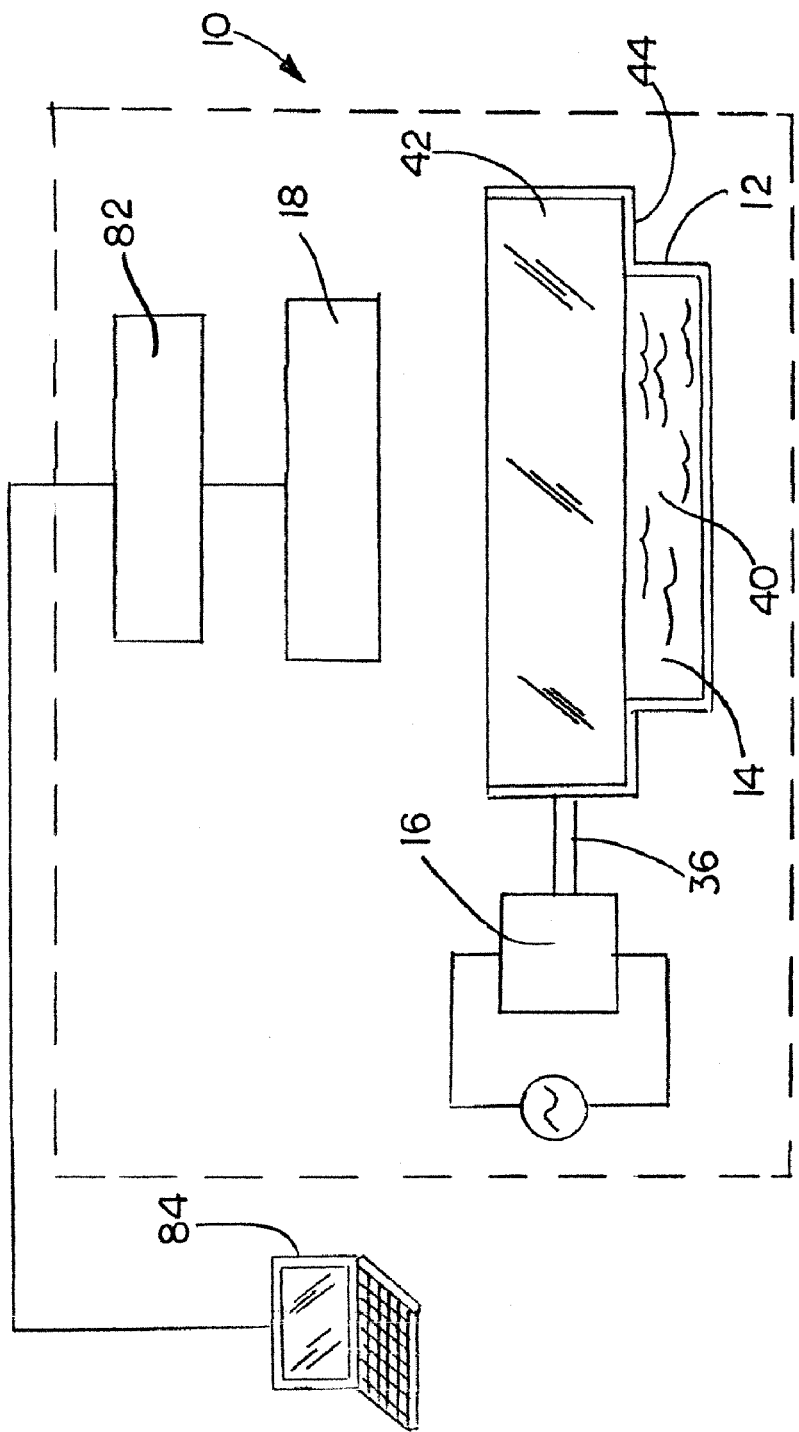
FIG. 6 is a schematic view of an analyzer in accordance with the teachings of the instant disclosure.
Figure 7:
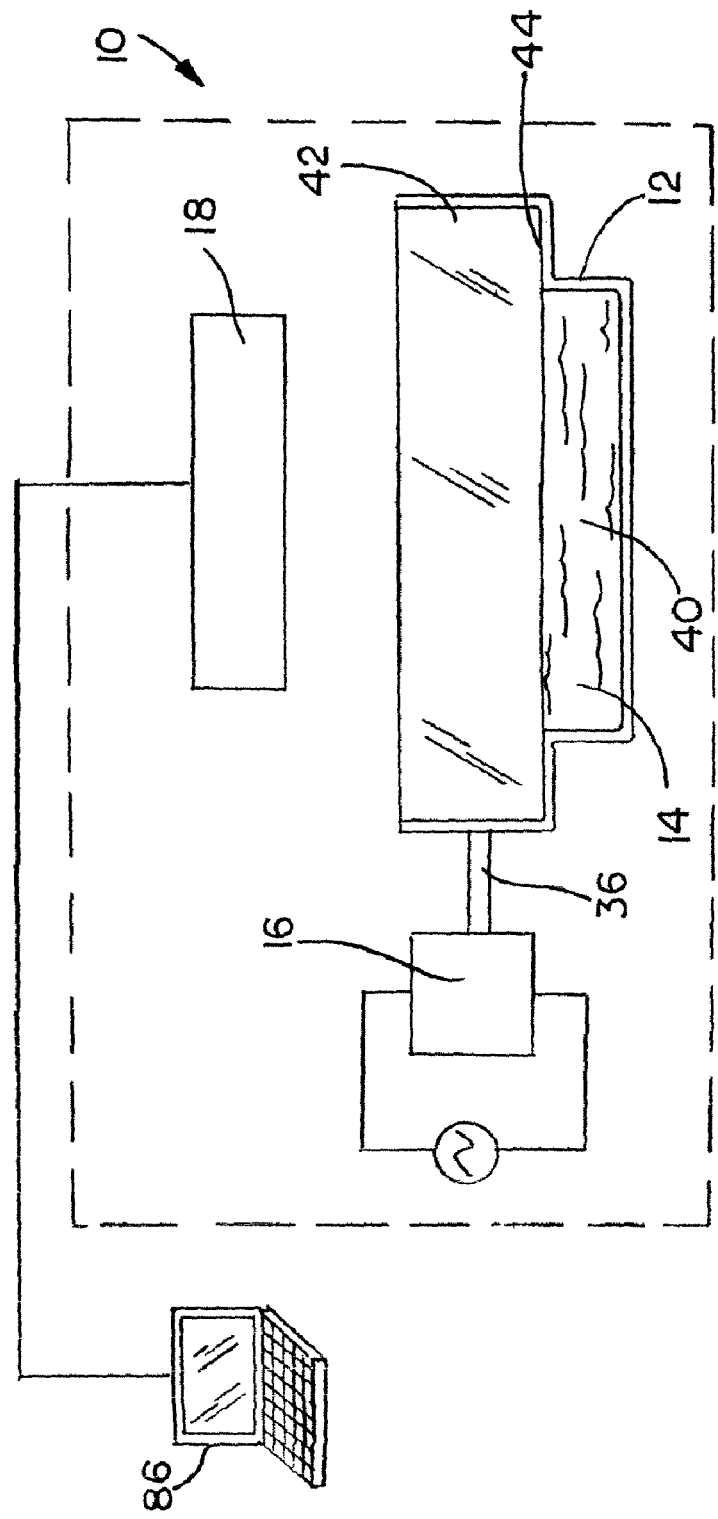
FIG. 7 is a schematic view of an analyzer in accordance with the teachings of the instant disclosure.

In others example of the present disclosure, the vibrations in the blood sample 14 may be measured by a number of other devices. In one example, acoustic sensors (not shown) disposed in the container 12 can differentially measure the distance from the surface of the blood sample 14 to the sensor, which is indicative of the vibration in the blood sample 14. In another example, electrodes (not shown) arranged in the container 12 function as either a capacitive or resistive bridge (i.e., a Wheatstone bridge). The voltage differential of the capacitors or the resistors is indicative of the vibrations of the blood sample 14. In yet another example, two photo diodes (not shown) can be placed on an interior wall of the container near the surface of the blood sample 14. As the blood sample 14 vibrates, it partially or fully obscures one or both of the diodes (i.e., preventing light from reaching the diodes). Accordingly, differential measurement of the outputs of the diodes identifies peaks in the displacement of the blood sample 14, which are indicative of resonance, can be identified One of ordinary skill in the art will appreciate the numerous methods and devices that can be used for driving the shaker 16 and analyzing the signals from the sensor 18 for determining the hemostasis characteristics of the blood sample 14. For instance, as shown in FIG. 5, the blood hemostasis analyzer 10 can include an internal computing device 80 that includes the necessary hardware and software to drive the shaker 16 independently or in response to signals from the sensor 18. Furthermore, the internal computing device 80 can analyze the signals from the sensor 18 to determine the fundamental natural frequencies of the blood sample 14 during hemostasis. As described in the foregoing, such an analysis will yield data for constructing the curves 30 and other data regarding the hemostasis characteristics of the blood sample 14. In another example as shown in FIG. 6, the analyzer 10 can include a memory device 82 for storing the data from the sensor 18 for later analysis by an external computing device 84. The shaker 10 can be driven by a predetermined method stored in the memory device 82, or by the external computing device 84. In yet another example shown in FIG. 7, the analyzer 10 does not include any internal memory or computing device. During testing, the analyzer 10 is in continuous and real-time communication with an external computing device 86 (e.g., laptop, personal digital assistant, desktop computer, etc.). The external computing device 86 drives the shaker 16 and receives signals from sensor 18 to determine the hemostasis characteristics of the blood sample 14 as described in the foregoing. One of ordinary skill in the art will appreciate that numerous other well known methods, algorithms and devices can be utilized to drive the shaker 16, independently or in response to signals from the sensor 18, and determine blood hemostasis characteristics from the sensor signals. Furthermore, the determined blood hemostasis characteristics can be conveyed to a user by a variety of well known methods and devices, such as displaying data on a display screen, or printing the results on paper.

One of ordinary skill in the art will appreciate that the foregoing generalized device is very rugged and not easily susceptible to damage from being mishandled. The disclosed device has a very small number of moving parts or parts that are breakable. Furthermore, the simplicity of the disclosed device provides for quick replacement of a defective part when necessary.

Figure 8:
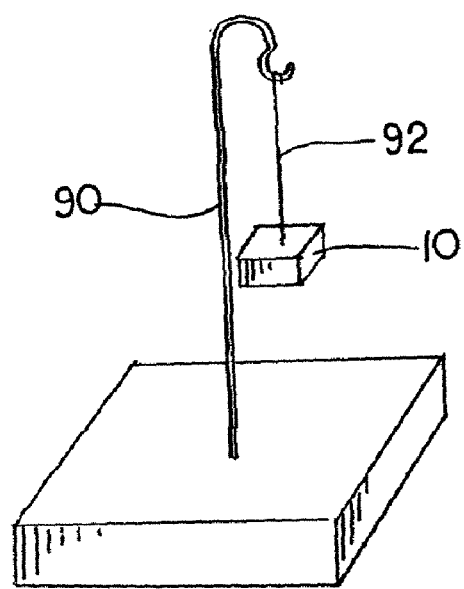
FIG. 8 is a perspective view of a first exemplary stand for a blood hemostasis analyzer constructed in accordance with the teachings of the instant disclosure.
Figure 9:
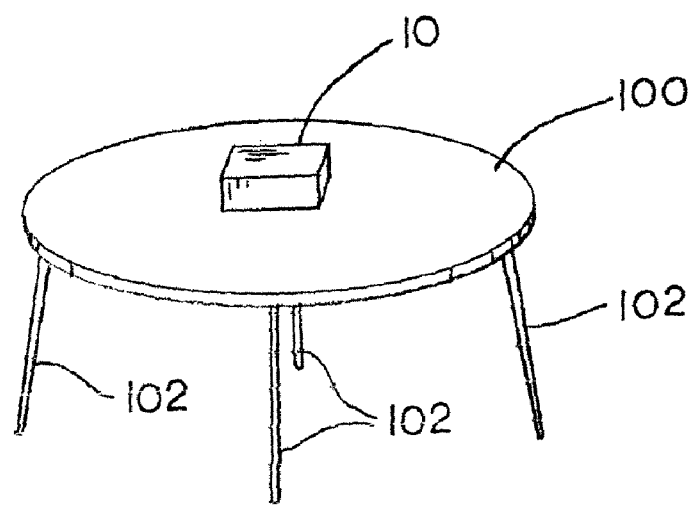
FIG. 9 is a perspective view of a second exemplary stand for a blood hemostasis analyzer constructed in accordance with the teachings of the instant disclosure.

Ambient vibrations or seismic noise near the analyzer 10 can disturb or influence the blood hemostasis analysis. Accordingly, the analyzer 10 can include a vibration filtering device onto which the analyzer 10 is mounted. In a first example as shown in FIG. 8, the vibration filtering device is a hook 90, from which the analyzer 10 is suspended by a cable 92. In effect, the analyzer 10 is suspended from the hook 90 in a pendulum-like manner. Seismic noise or ambient vibration in a wide range of frequencies is dissipated through the hook 90 and the cable 92 prior to reaching the analyzer 10. One of ordinary skill in the art will appreciate that any wire that is connected to the analyzer 10 for power or communication purposes can be carried by the cable 92 so as to not externally influence the motion of the analyzer 10 (e.g., hanging wires contacting other objects). In a second example as shown in FIG. 9, the seismic filtering device is a platform 100 that rests on a number of legs 102. In effect, the platform 100 is an inverted pendulum. In application, the analyzer 10 is placed on the platform 100 so that any ambient vibration or seismic noise within a wide frequency range is dissipated through the platform 100 prior to reaching the analyzer 10. One of ordinary skill in the art will appreciate many other ways of isolating noise, including use of vibration absorbing foams, spring suspension and the like.

As mentioned above, the container 12 is designed to retain the sample so that a relatively flat upper surface is formed. The flat upper surface facilitates reflection of the light beam during the oscillating/sloshing motion of the sample. Distortion of the upper surface may adversely affect measurement of the oscillating motion of the sample. A source of such distortions may be the sample itself. With fresh, whole blood, for example, serum may separate out from the sample during testing, and being of lower specific gravity, rises to the top of the sample. In doing so it does not disperse uniformly on the surface, but it tends to form into small liquid puddles. These serum puddles may adversely reduce the effectiveness of the optical sensor.

Figure 10:
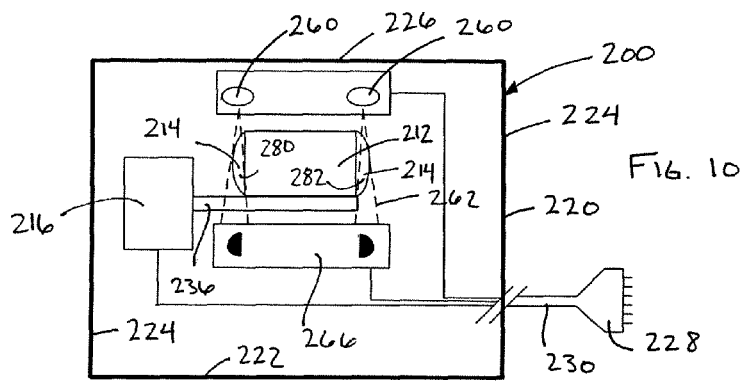
FIG. 10 is a schematic view of an analyzer in accordance with the teaching of the instant disclosure.

FIG. 10 illustrates another exemplary analyzer device 200 employing an observation of resonant motion of the sample method of determining hemostasis characteristics of a blood sample 214. The analyzer device 200, in contrast to the analyzer 100, does not rely upon maintaining a relatively flat sample surface and is therefore not susceptible to distortions of that surface, but instead uses a cylinder or ring with two open ends.

An outer housing 220 with a bottom surface 222 with side walls 224 and a top 226 encloses the operating components of the device 200. The outer housing 220 may optionally include a lid (not depicted) for providing access to the operating components through the top 226. Wiring 230 coupling to the various electrical components of the device 200 extends through one of the side walls 224 terminating in an electrical connector 228. The electrical connector 228 may be virtually any standard type connector, and for example, may be a Universal Serial Bus (USB) or similar type connector to allow the device 200 to be coupled to a computer or similar device. Furthermore, the device 200 may include a battery (not depicted) or may draw electrical power via the connector 228 from a host device. The device 200 itself may be relatively small, having length, width and height dimensions on the order of about 2 cm or less.

With continued reference to FIG. 10, a container 212 coupled to a shaker 216 are operably disposed and secured within the housing 220. The shaker 216 displaces the container 212 to excite a blood sample 214 contained by the container 212 to resonant vibration. Generally, the shaker 216 is a device capable of oscillating the container 212 with a desired frequency and amplitude. One of ordinary skill in the art will appreciate the numerous devices by which an object can be oscillated. In the disclosed example, the shaker 216 is a dipcoil, which is similar to a voice coil of a speaker. In other words, the shaker 216 includes an electromagnetic coil that oscillates relative to a stationary permanent magnet by having its coil current driven by an electrical signal. The shaker 216 may be connected either directly or with a connecting link 236 to the container 212. The connecting link 236 transfers the motion created by the shaker 216 to the container 212. To facilitate inserting a sample 214 into the device 200, the connecting link 236 may be formed with a socket, post or other feature to engage and retain the container 212. A handle, grip or other similar structure may further be provided on the container 212 to facilitate inserting and removal of the container 212 into and from the device 200.

The container 212 is oriented horizontally, and the shaker 216 is configured to excite the container in an axial oscillating motion. A pair of convex menisci 280 and 282 form at the end of the sample. As is well known to those of ordinary skill in the art, characteristics of the electrical signal, i.e., voltage, current, direction of current, etc., determine the characteristics of the oscillatory motion of the shaker 216. Accordingly, the shaker 216 can displace the container 212 with any desired amplitude and frequency within the operational limits of the shaker 216. As described above, a white noise excitation stimulus may be used. Excitation of the container 212 causes axial horizontal displacement of the sample 214, and corresponding displacement of the menisci 280 and 282. A light source 260, for example, an LED bulb light may direct a beam 262 at one or both of the menisci 280 and 282, and the movement of the menisci is detected by the interaction of the beam 262 with a sensor 266 that provides a signal of changing amplitude and frequency. Observation of changes in the oscillating motion of the sample 214, as reflected in the changing amplitude and frequency of the signal, as a result of changes in its natural frequency as the sample transforms from being substantially liquid to substantially solid and back again to substantially liquid, can be used to determine hemostatis characteristics. The apparatus 200 no longer requires maintaining a flat surface on the sample.

Figure 11:
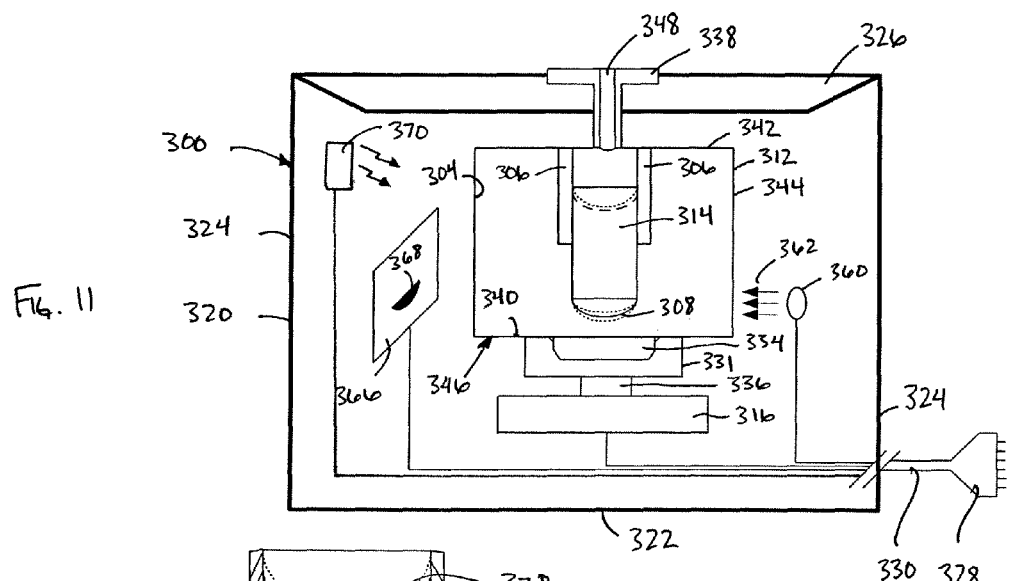
FIG. 11 is a schematic view of another analyzer in accordance with the teaching of the instant disclosure.

FIG. 11 illustrates another exemplary analyzer device 300 employing the observation of resonant motion of the sample method of determining hemostasis characteristics of a blood sample 314. The analyzer device 300 uses a cylinder or ring with open ends to hold the sample vertically with a convex meniscus forming at the lower end that is observable. In contrast to the analyzer 100, the analyzer device 300 does not rely upon maintaining a relatively flat sample surface and is therefore not susceptible to distortions of that surface.

An outer housing 320 with a bottom surface 322 with side walls 324 and a top 326 encloses the operating components of the device 200. The outer housing 320 may optionally include a lid (not depicted) for enclosing the top 326 and for providing access to the operating components and the sample container 312. Wiring 330 coupling to the various electrical components of the device 300 extends through one of the side walls 324 terminating in an electrical connector 328. The electrical connector 328 may be virtually any standard type connector, and for example, may be a Universal Serial Bus (USB) or similar type connector to allow the device 300 to be coupled to a computer or similar device. Furthermore, the device 300 may include a battery (not depicted) or may draw electrical power via the connector 328 from a host device. The device 300 itself may be relatively small, having length, width and height dimensions on the order of about 2 cm or less.

With continued reference to FIG. 11, a container 312 coupled to a shaker 316 are operably disposed and secured within the housing 320. The shaker 316 displaces the container 312 to excite a blood sample 314 contained by the container 312 to resonant vibration. Generally, the shaker 316 is a device capable of oscillating the container 312 with a desired frequency and amplitude. One of ordinary skill in the art will appreciate the numerous devices by which an object can be oscillated. In the disclosed example, the shaker 316 is a dipcoil, which is similar to a voice coil of a speaker. In other words, the shaker 316 includes an electromagnetic coil that oscillates relative to a stationary permanent magnet by having its current driven by an electrical signal. The shaker 316 may be connected either directly or with a connecting link 336 to the container 312. The connecting link 336 transfers the motion created by the shaker 316 to the container 312. To facilitate inserting a sample 314 into the device 300, the connecting link 336 may be formed with a socket portion 331 that includes a bore 332 into which a post 334 formed on the container 312 is inserted. Frictional engagement of the post 334 with the bore 332 retains the container 312 to the shaker 316 and hence within the device 300 although a mechanical coupling, detent or other suitable mechanism may be employed to ensure the container 312 remains secured to the device 300 during testing. A handle, grip or other similar structure 338 may further be formed on the container 312 to facilitate inserting and removal of the container 312 into the device 300.

As is well known to those of ordinary skill in the art, characteristics of the electrical signal, i.e., voltage, current, direction of current, etc., determine the characteristics of the oscillatory motion of the shaker 316. Accordingly, the shaker 316 can displace the container 312 with any desired amplitude and frequency within the operational limits of the shaker 316. For example, a white noise excitation stimulus may be used.

Ideally, the blood sample would be maintained as a free floating drop in order to result in a highest Q factor, that is, the lowest damping. Successful Eigenfrequency measurement determines the need for a high Q resonance with a sharp definition of the frequency at the peak. As the peak changes in time with the changing modulus of elasticity of the blood sample 314 as it coagulates and lyses, the device 300 or a coupled computing device controlling operation of the device 300 is operable to find the new resonances using suitable analysis techniques, such as Fast Fourier Transform (FFT) analysis. High Q is desirable because the methodology seeks a resonance frequency that represents the modulus of elasticity. This is the same goal of previous resonant hemostasis analysis devices, to deliver in time the changing modulus of elasticity of the blood sample as a result of hemostasis. A high Q, low damping blood sample design ensures that as the sample is excited, e.g., vibrated, oscillated, sloshed, etc., the spectrum will show a sharp peak with minimal width at resonance.

FIG. 11 illustrates the container 312 as including an open ended cylinder or ring 302 supported vertically within outer walls 304 by supports 306 such that the blood sample takes on the desired shape of having a convex meniscus at the bottom end. While shown as separate support members, the supports 306 may be a single annular cylinder into which the cylinder 302 is secured. The cylinder 302 may take on other shapes and sizes. The shape and size of the container and particularly the cylinder 302 may affect the operation of the analyzer device 300, because the container 312 and particularly the cylinder 302 act as a resonator. The larger the cylinder 302, the lower the natural frequency of the blood sample 314 will be. The diameter of the cylinder 302 is sized to cause the cylinder 302 to retain the blood sample 314 therein by surface tension. As such the blood sample 314 forms a column within the cylinder 302 with an unsupported bottom surface 308 taking on a convex shape. Thus, the cylinder 302 is small enough to form the surface 308 yet not so large that either a large blood sample 314 will be needed for the analysis in the analyzer device 300, which may not be medically acceptable, or so that the blood sample 314 is easily displaced from the cylinder 302 during excitation, handling or accidental acceleration due to dropping of the container 312 or the like. In this regard, the inside diameter of the cylinder 302 may be from about 2 mm to about 5 mm. The shaker 316 causes displacement of the container 312 and the cylinder 302 substantially along the axis of the cylinder 302, and hence, the axis of the column formed by the blood sample 314.

The container 312 has a lower wall 340, an upper wall 342 and a sidewall 344 defining an enclosure 346 for the cylinder 302. The planar lower and upper walls 340 and 342 enclose the volume defined by the side wall 344. The enclosure 346 may be cubic, as illustrated by the rectangular representation of the side wall 344; however, the enclosure 346 may be cylindrical or any other suitable shape. The enclosure 346 may also be sealed against accidental spillage of the blood sample 314 should it become dislodged from the cylinder 302, and further provides for safe disposal of the blood sample 314 following testing. The supports 306 may be integrated with the wall 344 or otherwise formed with the container 312. A port 348 is provided at a suitable location on the container 312 to allow introduction of the blood sample 314 into the cylinder 302. The container 312 and all of its constituent parts may be fabricated from a suitable grade of medical plastic.

To prevent the blood sample 14 from evaporating during testing and to prevent contamination thereof, the port 348 may be self sealing. For example, the port 348 may be constructed from rubber or silicon so that when a cannula, such as syringe needle, pipette, or other such, preferably blunt tipped device, is inserted therein, the rubber or silicon resiliently surrounds the cannula to substantially seal the port during the injection of the blood sample 314 into the cylinder 302. When the cannula is withdrawn from the port 348, resilience of the rubber or the silicon substantially re-seals the hole created by the cannula thereby resealing the port 348. Also to prevent evaporation of the blood sample 314 and any reaction the blood sample may have by being exposed to dry air, the container 312 can be pre-filled with humid air produced by a water droplet or water vapor. Alternately, the air in the container 312 can be removed to provide a vacuum inside the container 312. One of ordinary skill in the art will recognize that the pressure in the container 312 has minimal to no effect on the fundamental natural frequency of the blood sample 314. Furthermore, it is believed air within the container 312 has a minimal effect on hemostasis and no effect on the fundamental natural frequency of the blood sample 314. Thus, while the aforementioned precautions are possible to preserve the blood sample 314, they are not believed necessary to obtaining adequate performance.

In the example disclosed herein, the container 312 is safely disposable and can be safely discarded after each use. The disposability of the container 312 ensures that the blood sample 314 is safely handled during testing and safely discarded after testing. In addition, the disposable container 312 can be manufactured to be completely sealed and only provide access thereto by the port 348. Thus, the disposability of the container 312, combined with the container 312 being completely sealed, ensure that the blood sample 314 is not exposed to environmental conditions or any other contaminants, and furthermore, ensure safety in handling and disposing of the blood sample 314 before, during, and after testing.

Other environmental consideration of the device 300 includes providing a heat source 370 and a temperature sensor so that the sample may be maintained at an appropriate temperature during testing. The temperature sensor (not depicted) may also be provided to measure and provide a feedback signal that the blood sample 314 is being maintained at the desired temperature and to affect control of the heat source 370.

To measure oscillations of the blood sample 314 as a result of the displacement of the container 312, a fixed electromagnetic source 360 emits a beam 362 toward the blood sample 314, and particularly toward the surface 308. The source 360 may be part of the sensor that includes a detector, or as shown in FIG. 1, the source 360 and a sensor 366 can be independent devices disposed and secured within the housing 320. The beam 362 is detected by the sensor 366 after interacting with the surface 308 of the blood sample 314. The characteristics of the beam after interacting with the surface 308 of the blood sample 314 are indicative of the movement or displacement of the surface 308 and blood sample 314 in response to displacements of the container 312.

One of ordinary skill in the art will appreciate that the electromagnetic beam of the source 360 may be produced by any emission within the electromagnetic spectrum so long as the beam 362 can interact with the surface 308 of the blood sample 314 and provide a detectable characteristic representative of the movement and/or displacement of the surface 308 due to excitation of the container 312.

Figure 12:
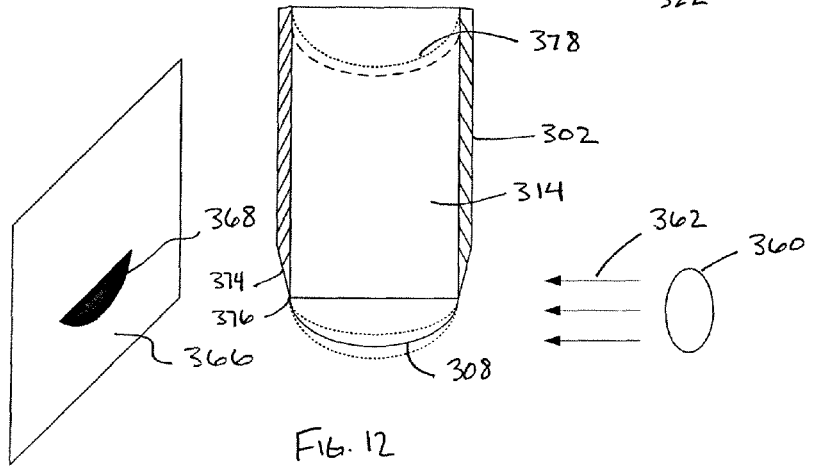
FIG. 12 is an enlarged schematic view of the analyzer illustrated in FIG. 11.

In the disclosed example, the source 360 is a LED (Light Emitting Diode) source that directs a light beam 362 towards the blood sample 314 and particularly the surface 308. The beam 362 obstructed by the surface 308 of the blood sample 314 resulting in a portion of the beam 362 arriving at the sensor 366, but also resulting in a discernable shadow 368 representing the convex shape of the surface 308 (FIG. 12). The sensor 366 may be photodiode or a collection or array of photodiodes, or any other suitable device for detecting the unshadowed portion of the beam 362. The container 312 furthermore has an optically portion transparent portion so the beam 362 can enter and exit the container 212, respectively. In the disclosed example, the wall 344 is transparent to light. One of ordinary skill in the art will recognize that the wall 344, although transparent, will itself reflect some of the light in the beam 362. To reduce the reflection of light from the wall 344, an anti-reflective coating may be applied to the wall 344. Such anti-reflective coatings are well known to those of ordinary skill in the art as they are applied to a variety of optical devices, such as eyeglasses, telescopes, cameras, etc. The surface of blood forms a dark surface so that most of the beam 362 incident on the surface 308 is blocked by the surface 308 from the reaching sensor 366 resulting in a shadow being formed on the sensor 366. As the beam 362 need only interact with the surface 308, which because it is convex extends from outside the cylinder 302, the cylinder 302 need not be transparent, but can be opaque as is convenient to manufacture.

Referring to FIG. 12, the displacements of the blood sample 314, and particularly the surface 308 relative to a rest position are shown with dashed lines 372. The cylinder 302 has two open ends, with the upper menisci being concave and the lower meniscus being convex (surface 308). The lower end may be formed with a chamfered surface 374 defining a sharp edge 378 to reduce surface tension affects that may adversely affect formation of the meniscus. The sensor 366 may be a simple shadow meter. The light beam 362 aimed at the surface 308 casts as shadow 364 on the sensor 366. As the surface 308 is excited, and oscillates, extending farther from the ring 302 and contracting toward the ring 302, the size of the shadow correspondingly becomes larger and smaller. This results in an alternating current (AC) output from the sensor 366 corresponding to the size of the shadow. The AC signal is representative of the amplitude and frequency of the vibrating sample 314, which allows determination of the resonance frequency of the blood sample 314. The resonance frequency is related to the modulus of elasticity of the blood sample 314, which changes as the blood sample 314 coagulates and subsequently lyses.

In other examples of the present disclosure, the vibrations in the blood sample 314 may be measured by a number of other devices. In one example, acoustic sensors (not shown) disposed in the container 312 can differentially measure the distance from the surface 308 of the blood sample 314 to the sensor, which is indicative of the vibration in the blood sample 314. In another example, electrodes (not shown) arranged in the container 312 function as either a capacitive or resistive bridge (i.e., a Wheatstone bridge). The voltage differential of the capacitors or the resistors is indicative of the displacement of the surface 308 of the blood sample 314. In yet another example, any array of photo diodes (not shown) can be placed on an interior wall of the container near the surface 308 of the blood sample 314. As the blood sample 314 vibrates, it partially or fully obscures a portion of the plurality of the diodes (i.e., preventing light from reaching the diodes).

The arrangement of the analyzer 300 depicted in FIGS. 11 and 12 advantageously avoid problems with blood separation that may occur, for example, when testing fresh whole blood samples. As noted above in connection with the analyzer 100, separation of serum from the sample and its subsequent puddling on the surface of the sample 14 can adversely affect the ability to measure the sloshing motion of the sample. Retaining the sample 314 vertically in the cylinder 302, and observing only the bottom surface 308 eliminates the possibility of serum (e.g., serum 378) puddling on the surface being observed.

Although certain apparatus constructed in accordance with the teachings of the invention have been described herein, the scope of coverage of this patent is not limited thereto. Generally, apparatus and methods are provided yielding first time continuous, accurate results starting from fresh liquid blood and all along the transition to solid vibrating coagulant. Observation of the increasing Eigenfrequency of the coagulant provides a direct measure of hemostasis. On the contrary, this patent covers all examples of the teachings of the invention fairly falling within the scope of the appended claims either literally or under the doctrine of equivalents.

What is claimed is:

1. An apparatus for measuring hemostasis comprising:
   a container adapted to hold a blood sample such that a surface of the blood sample is substantially unconstrained in one direction;
   a shaker adapted to displace the container in order to cause an excitation of the blood sample and corresponding resonant displacement of the surface along the one direction; and
   a sensor adapted to determine the resonant displacement of the surface along the one direction, wherein the direction is vertical and the surface is a bottom surface of the blood sample.

2. A method for measuring hemostasis comprising:
   providing a blood sample;
   exciting the blood sample to a resonant state by displacing the blood sample to create displacement of a surface of the blood sample in a direction;
   observing the amplitude and frequency of the displacement of the surface of the blood sample;
   determining a resonant frequency of the blood sample to provide a plurality of resonant frequencies of the blood sample based upon the observed amplitude and frequency of the surface; and
   deriving a hemostasis characteristic of the blood sample from the plurality of resonant frequencies of the blood sample.

3. A method according to claim 2, further comprising displacing the blood sample at a frequency, and incrementally varying the frequency until a resonant frequency of the blood sample is determined.

4. A method according to claim 2, wherein displacing the blood sample comprises displacing the blood sample a at displacement frequency, the method further comprising incrementally varying the displacement frequency to determine the plurality of resonant frequencies of the blood sample before, during and after hemostasis of the blood sample, wherein the plurality of the resonant frequencies are indicative of the hemostasis characteristics of the blood sample.

5. A method according to claim 2, further comprising:
displacing the blood sample with a frequency function, the frequency function having frequency components, and the frequency components being selected from a range of frequencies; and
determining a plurality of resonant frequencies of the blood sample before, during and after hemostasis of the blood sample;
wherein the plurality of the resonant frequencies are indicative of the hemostasis characteristics of the blood sample.

6. A method according to claim 2, wherein the blood sample is supported in a column, the surface comprising a bottom surface of the column and step of displacing the sample comprises displacing the sample along an axis of the column.

7. A method according to claim 2, comprising placing the blood sample in a container by injecting the blood into the container through a self-sealing port on the container.

8. A method according to claim 2, wherein the determining a resonant frequency of the blood sample comprises either continuously determining a change in resonant frequency with time or periodically determining the resonant frequency.

* * * * *